United States Patent [19]

Jarvi et al.

[11] Patent Number: 5,521,162
[45] Date of Patent: May 28, 1996

[54] ARISTEROMYCIN ANALOGUES OF 4',5'-DIDEHYDRO-5'-FLUORO-ADENOSINE AND METHODS OF TREATING NEOPLASTIC AND VIRAL DISEASE CONDITIONS

[75] Inventors: Esa T. Jarvi, Cincinnati; James R. McCarthy, West Chester; Nellikunja J. Prakash, Cincinnati, all of Ohio

[73] Assignee: Merrell Pharmaceuticals Inc., Cincinnati, Ohio

[21] Appl. No.: 333,116

[22] Filed: Nov. 1, 1994

Related U.S. Application Data

[63] Continuation of Ser. No. 201,145, Feb. 24, 1994, abandoned, which is a continuation of Ser. No. 99,111, Jul. 29, 1993, abandoned, which is a continuation-in-part of Ser. No. 62,694, May 17, 1993, abandoned, which is a continuation of Ser. No. 918,910, Jul. 23, 1992, abandoned, which is a continuation of Ser. No. 803,773, Dec. 5, 1991, abandoned, which is a continuation of Ser. No. 626,090, Dec. 11, 1990, abandoned, which is a division of Ser. No. 445,892, Nov. 29, 1989, Pat. No. 4,997,924, which is a continuation of Ser. No. 89,693, Aug. 26, 1987, abandoned.

[51] Int. Cl.⁶ ................. A61K 31/70; A61K 31/675; C07D 487/00
[52] U.S. Cl. ................. 514/46; 514/45; 514/81; 536/27.14; 536/27.4; 536/29.2; 544/262
[58] Field of Search ................. 536/27.14, 27.4, 536/29.2; 514/45, 46, 81; 544/262

[56] References Cited

U.S. PATENT DOCUMENTS

| | | | |
|---|---|---|---|
| 3,472,837 | 10/1969 | Verheyden et al. | 536/27.5 |
| 3,825,541 | 7/1974 | Vince et al. | 544/277 |
| 3,910,885 | 10/1975 | Moffatt et al. | 536/27.5 |
| 4,321,376 | 3/1982 | Otani et al. | 544/277 |
| 4,386,093 | 5/1983 | Chiang et al. | 424/256 |
| 4,387,228 | 6/1983 | Montgomery et al. | 546/118 |
| 4,423,218 | 12/1983 | Otani et al. | 544/277 |
| 4,728,736 | 3/1988 | Shealy et al. | 544/254 |
| 4,816,575 | 3/1989 | Fukukawa et al. | 544/277 |
| 4,916,224 | 4/1990 | Vince et al. | 544/254 |
| 4,954,504 | 9/1990 | Chen et al. | 514/265 |
| 4,968,690 | 11/1990 | Marquez et al. | 514/303 |

FOREIGN PATENT DOCUMENTS

| | | | |
|---|---|---|---|
| 0277599 | 8/1988 | European Pat. Off. | 536/27.4 |
| 0347852 | 12/1989 | European Pat. Off. | 544/277 |
| 0366385 | 5/1990 | European Pat. Off. | 536/27.14 |
| 1113851 | 5/1968 | United Kingdom | 536/27.5 |

OTHER PUBLICATIONS

Ferrier, "4',5'-Unsaturated Cyclic Compounds," *Advances in Carbohydrate Chemistry and Biochemistry*, 24, 250–251 (1969).

Bennett et al., "Differences in the Metabolism and Metabolic Effects of the Carbocyclic Adenosine Analogs, Neplanocin A and Aristeromycin," *Mol. Pharmacol.*, 29, 383–390 (1986).

DeClercq, "S-Adenosylhomocysteine Hydrolase Inhibitors as Broad Spectrum Antiviral Agents," *Biochem. Pharmacology*, 36, 2567–2575 (1987).

Brimacombe, "The Synthesis of Rare Sugars," *Angewandte Chemie. Intl. Ed.*, 8(6), 401–468 (1969).

Cook et al., "Nucleoside 4',5'-Enol Acetates. Synthesis and Chemistry of a Unique Uridine $O^2$, 4'-Anhydronucleoside," *J. Am. Chem. Soc.*, 101, 1554–1564 (1979).

Jenkins et al., "4'-Substituted Nucleosides. 2. Synthesis of the Nucleoside Antibiotic Nucleocidin," *J. Am. Chem. Soc.*, 98(11), 3346–3357 (1976).

Richards et al., "Synthesis of 4'-Methoxyadenosine and Related Compounds," *Carbohydrate Research*, 100, 315–329 (1982).

Verheyden et al., "Synthesis of Certain 4'-Substituted Nucleosides," *Ann. N.Y. Acad. Sci.*, 225, 151–165 (1975).

Aarbakke et al., "Induction of HL-60 Cell Differentiation by 3-Deaza(±)-Aristeromycin, an Inhibitor of S-Adenosylhomocysteine Hydrolase," *Cancer Res.*, 46, 5469–5472 (1986).

Montgomery et al., "Carbocyclic Analogue of 3-Deazaadenosine: A Novel Antiviral Agent Using S-Adenosylhomocystgeine Hydrolase as a Pharmacological Target," *J. Med. Chem.*, 25, 626–629 (1982).

DeClercq et al., "Broad-Spectrum Antiviral Activity of the Carbocyclic Analog of 3-Deazaadenosine," *Antiviral Res.*, 3, 17–24 (1983).

Baker et al, "5'-Substituted-5'-Deoxy Nucleosides," *Tetrahedron*, 30, 2939–2942 (1974).

Craig et al., "Synthesis of 9-[5-(Alkylthio)-5-deoxy-β-D-erythro-pent-4-enofuranosyl)adenines as Potential Inhibitors of Transmethylation," *J. Org. Chem.* 51, 1258–1264 (1986).

Palmer et al., "The Mechanism of Action of S-Adenosylhomocyteinase," *J. Biol. Chem.*, 254(4), 1217–1225 (1979).

Primary Examiner—Douglas W. Robinson
Assistant Examiner—L. Eric Crane
Attorney, Agent, or Firm—Louis J. Wille

[57] ABSTRACT

This invention relates to certain aristeromycin/adenosine derivatives which are useful in inhibiting AdoMet-dependent transmethylation and in the treatment of patients afflicted with neoplastic or viral disease states.

31 Claims, No Drawings

ARISTEROMYCIN ANALOGUES OF 4',5'-DIDEHYDRO-5'-FLUORO-ADENOSINE AND METHODS OF TREATING NEOPLASTIC AND VIRAL DISEASE CONDITIONS

CROSS-REFERENCE TO RELATED APPLICATION

This is a continuation of application Ser. No. 08/201,145, filed Feb. 24, 1994 now abandoned; which is a continuation of application Ser. No. 08/099,111 filed Jul. 29, 1993, now abandoned; which is a continuation-in-part of application Ser. No. 08/062,694, filed May 17, 1993, now abandoned; which is a continuation of application Ser. No. 07/918,910, filed Jul. 23, 1992, now abandoned; which is a continuation of application Ser. No. 07/803,773, filed Dec. 5, 1991, now abandoned; which is a continuation of application Ser. No. 07/626,090, filed Dec. 11, 1990, now abandoned; which is a divisional of application Ser. No. 07/445,892, filed Nov. 29, 1989, now U.S. Pat. No. 4,997,924; which is a continuation of application Ser. No. 07/089,693, filed Aug. 26, 1987, now abandoned, which is herein incorporated by reference.

BACKGROUND OF THE INVENTION

S-Adenosyl-L-methionine (AdoMet) dependent transmethylation reactions have been implicated in a variety of biological processes related to vital growth and replication, vital transformation of cells, growth of malignant cells, and processes such as chemotaxis and secretion [See P. M. Ueland, Pharm. Reviews, 34, 223 (1982)]. In general, these transmethylation reactions are catalyzed by various transmethylases which utilize AdoMet as a methyl-donor substrate in the methylation of a number of methyl-acceptor substrates such as catechols; norepinephrine; histamine; serotonin; tryptamine; membrane phospholipids; lysyl, arginyl, histidyl, aspartyl, glutamyl, and carboxyl groups of certain proteins; tRNA and mRNA; and DNA. These various transmethylases produce S-Adenosine-L-Homocysteine (AdoHcy) as a byproduct upon transfer of a methyl group from AdoMet to the appropriate methyl-acceptor substrate.

AdoHcy has been shown to be a potent feed-back inhibitor of the AdoMet-dependent transmethylation reactions. This feed-back inhibition of the transmethylases is controlled by the biodegradation of AdoHcy by S-Adenosyl-L-Homocysteine Hydrolase which provides a homeostatic control on the tissue levels of AdoHcy. The activity of S-Adenosyl-L-Homocysteine Hydrolase is generally considered by those skilled in the art to play an important role in regulating the tissue levels of AdoHcy and thereby controlling the activity of the AdoMet dependent transmethylation reactions.

The compounds of the present invention are inhibitors of S-Adenosyl-L-Homocysteine Hydrolase. These compounds therefore inhibit the naturally-occurring biodegradation of AdoHcy and result in elevated tissue levels of AdoHcy. Elevated levels of AdoHcy in turn provide an endogenous feed-back inhibition of various AdoMet dependent transmethylation reactions which are associated with biological processes related to viral growth and replication, viral transformation of cells, growth of malignant cells, and processes such as chemotaxis and secretion. The compounds of the present invention are therefore useful as inhibitors of these biological processes and useful in an end use application as therapeutic agents in the treatment of patients afflicted with various pathological conditions in which these processes are implicated, such as, viral infections and neoplastic disease states.

SUMMARY OF THE INVENTION

The present invention relates to novel aristeromycin/adenosine derivatives which are useful as inhibitors of S-Adenosyl-L-Homocysteine Hydrolase and are useful as anti-vital and anti-neoplastic agents.

The present invention provides novel aristeromycin/adenosine derivatives of the formula (1)

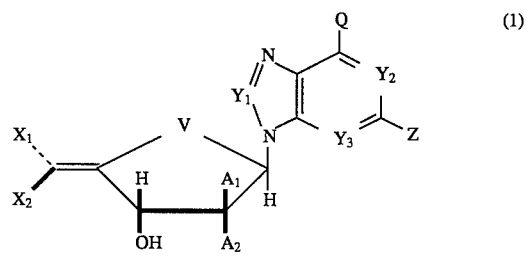

wherein

V is oxy or methylene, $X_1$ and $X_2$ are each independently hydrogen or halogen with the proviso that at least one of $X_1$ and $X_2$ is always a halogen atom, $A_1$ and $A_2$ are each independently hydrogen, halogen, or hydroxy with the provisos that where $A_1$ is hydroxy, $A_2$ is hydrogen, and that where $A_2$ is hydroxy, $A_1$ is hydrogen, $Y_1$ is nitrogen, a CH group, a CCl group, a CBr group or a $CNH_2$ group, $Y_2$ and $Y_3$ are each independently nitrogen or a CH group, Q is $NH_2$, NHOH, $NHCH_3$, or hydrogen, and Z is hydrogen, halogen, or $NH_2$; or a pharmaceutically acceptable salt thereof.

The present invention also provides a method of inhibiting AdoMet-dependent transmethylation activity in a patient in need thereof comprising administration of a therapeutically effective inhibitory amount of a compound of formula (1).

Another embodiment of the present invention is a method of treating a patient afflicted with a neoplastic disease state or in controlling the growth of a neoplasm in a patient afflicted with a neoplastic disease state comprising administration of a therapeutically effective antineoplastic dose of a compound of formula (1).

A further embodiment of the present invention is a method of treating a patient afflicted with a viral infection or of controlling a viral infection in a patient afflicted therewith comprising administration of a therapeutically effective antiviral amount of a compound of formula (1).

DETAILED DESCRIPTION OF THE INVENTION

As used herein, the term "halogen" or "$X_{Hal}$" refers to a fluorine, chlorine, bromine, or iodine atom and the term "nitrogen" refers to a trivalent nitrogen atom attached to two radicals.

The aristeromycin/adenosine derivatives of the formula (1) wherein either $X_1$ or $X_2$ is hydrogen can be prepared by utilizing procedures and techniques well known and appreciated by one of ordinary skill in the art. A general synthetic procedure is set forth in Scheme A wherein all substituents, unless otherwise indicated, are as previously defined.

blocking groups can be conventional amino protecting

SCHEME A

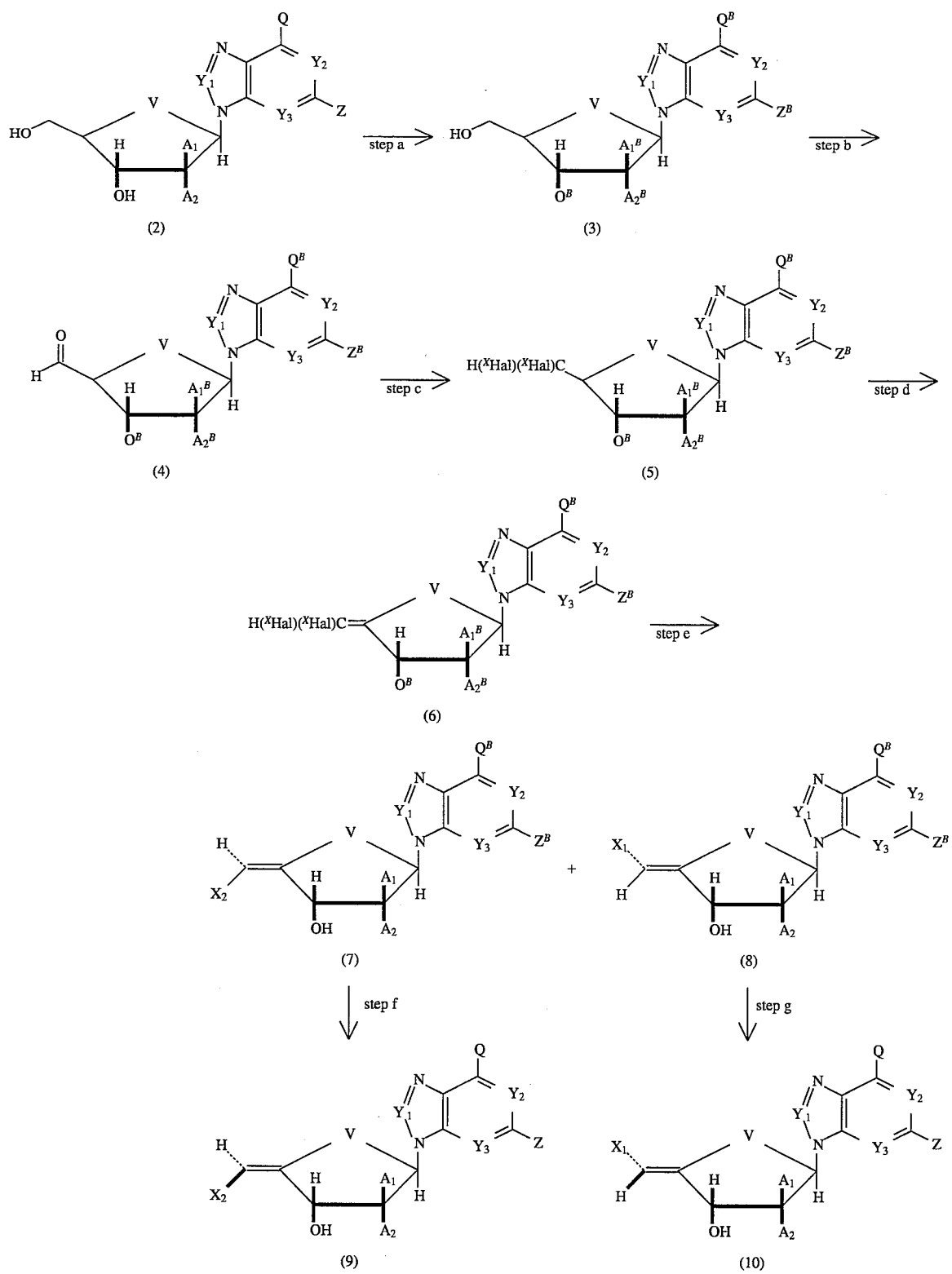

Basically, in step a, reactive hydroxy, amino, or hydroxylamino groups other than the 5'-hydroxy group are blocked with standard blocking agents well known in the art. These blocking groups can be conventional amino protecting groups for Q and Z (wherein Q or Z are $NH_2$) and conventional hydroxy protecting groups for the 3'-hydroxy, for $A_1$ or $A_2$ (wherein $A_1$ or $A_2$ are OH), and for Q (wherein Q is hydroxylamino). $O^B$, $A_1^B$, $A_2^B$, $Q^B$ and $Z^B$ in Scheme A represent the 3'-hydroxy, $A_1$, $A_2$, Q, and Z groups as herein defined blocked with a blocking group where appropriate.

The selection and utilization of particular blocking groups are well known to one of ordinary skill in the art. In general, blocking groups should be selected which adequately protect the amino or hydroxy groups in question during subsequent synthetic steps and which are readily removable under conditions which will not cause degradation of the desired product.

Examples of suitable hydroxy protecting groups are $C_1$–$C_6$ alkyl, tetrahydropyranyl, methoxymethyl, methoxyethoxymethyl, t-butyl, benzyl, and triphenylmethyl. The term $C_1$–$C_6$ alkyl refers to a saturated hydrocarbyl radical of one to six carbon atoms of straight, branched, or cyclic configuration. The preferred blocking group for the 3'-hydroxy and for $A_2$ (wherein $A_2$ is hydroxy) is 2',3'-0-isopropylidene formed by reacting the unblocked compound with acetone.

Examples of suitable amino protecting groups are benzoyl, formyl, acetyl, trifluoroacetyl, phthalyl, tosyl, benzenesulfonyl, benzyloxycarbonyl, substituted-benzyloxycarbonyl (e.g., p-chloro, p-bromo, p-nitro, p-methoxy, o-chloro, 2,4-dichloro, and 2,6-dichloro derivatives), t-butyloxycarbonyl (Boc), t-amyloxycarbonyl, isopropyloxycarbonyl, 2-(p-biphenyl)-isopropyloxycarbonyl, allyloxycarbonyl, cyclopentyloxycarbonyl, cyclohexyloxycarbonyl, adamantyloxycarbonyl, phenylthiocarbonyl, and triphenylmethyl. The preferred amino protecting group is the di-benzoyl derivative made by reacting the unblocked compound with benzoyl chloride.

In step b, the appropriately blocked 5'-hydroxy derivative (3) is oxidized to the corresponding aldehyde (4). The preferred oxidizing reagent is dicyclohexylcarbodiimide, methyl phosphonic or dichloroacetic acid and dimethylsulfoxide.

The aldehyde (4) can optionally be derivatized so as to improve the handling characteristics of the compound or to facilitate purification thereof by means of procedures and techniques well known and appreciated in the art. For example, the 5',5'-(N,N'-diphenylethylenediamino) derivative can be prepared by the method of Ranganathan et al. (J. Org. Chem., 39, 290 (1974)].

In step c, the 5',5'-di-halo (i.e., "$X_{(Hal)}$ $(X_{Hal})$C") derivative (5) is formed by reacting the corresponding aldehyde (4) with diethylaminosulfur trihalide or similar halo-substituting reagent. Diethylaminosulfur trihalide is preferred.

In step d, the 5'-di-halo derivative (5) is dehydrohalogenated to form the unsaturated (i.e., "(H)($X_{Hal}$)C") derivative (6). The preferred reagent to effect the dehydrohalogenation is potassium t-butoxide in the presence of dimethylsulfoxide.

In step e, the hydroxy protecting groups are removed according to conventional procedures and techniques well known and appreciated in the art. For example, the 2',3'-0-isopropylidene blocking group can be removed by reacting (6) with aqueous trifluroacetic acid. The (Z) and (E) isomers, i.e., (7) and (8), respectively, can conventionally be isolated at this stage of the synthesis by the utilization of conventional isolation techniques as are well known and appreciated in the art. Alternatively, the (Z) and (E) isomers can be isolated after deblocking the amino-protecting groups as described below for steps f and g.

In steps f and g, the amino-protecting groups of the (Z) and (E) isomers, i.e., (7) and (8) respectively, are removed utilizing procedures and techniques well known and appreciated in the art. For example, the benzoyl amino blocking groups can be removed by hydrolysis with ammonia.

Starting materials for use in the general synthetic procedure outlined in Scheme A are readily available to one of ordinary skill in the art. For example, certain starting materials for various compounds of formula (1) are listed in Table 1.

TABLE 1

Examples of Starting Materials for Scheme A
Compound of formula (1) wherein

| V | $A_1$ | $A_2$ | $Y_1$ | $Y_2$ | $Y_3$ | Z | Q | Source of Starting Material |
|---|---|---|---|---|---|---|---|---|
| O | H | OH | CH | N | CH | H | $NH_2$ | J. Med. Chem. 25, 626(1982) |
| O | OH | H | CH | N | N | H | $NH_2$ | Het. Chem. 14, 195(1977) |
| $CH_2$ | H | OH | CH | N | N | H | $NH_2$ | JACS 88, 3885 (1966) |
| O | H | H | CH | N | N | H | $NH_2$ | 2'-Deoxyadenosine (commercially available) |
| $CH_2$ | H | OH | CH | N | CH | H | $NH_2$ | J. Med. Chem. 2.5 626(1982) |
| O | OH | H | CH | N | N | F | $NH_2$ | JACS 86, 1242 (1964) |
| O | H | OH | CH | CH | N | H | $NH_2$ | Nucleosides & Nucleotides, 1985, p. 625 |
| $CH_2$ | H | OH | CH | N | N | H | $NH_2$ | J. Pharm. Sci. 62 1252(1973) |
| $CH_2$ | H | $CH_2$ | CH | N | N | $NH_2$ | $NH_2$ | J. Med. Chem. 27 670(1984) |
| $CH_2$ | H | H | CH | N | N | H | $NH_2$ | J. Med. Chem. 27, 1416(1984) |
| $CH_2$ | OH | H | CH | N | N | H | $NH_2$ | J. Med. Chem. 27 1612(1977) |
| $CH_2$ | H | OH | N | N | N | H | $NH_2$ | J. Het. Chem.10, 1601(1973) |

TABLE 1-continued

Examples of Starting Materials for Scheme A
Compound of formula (1) wherein

| V | $A_1$ | $A_2$ | $Y_1$ | $Y_2$ | $Y_3$ | Z | Q | Source of Starting Material |
|---|---|---|---|---|---|---|---|---|
| $CH_2$ | H | H | N | N | N | $NH_2$ | $NH_2$ | J. Med. Chem. 27, 1416(1984) |
| $CH_2$ | H | H | N | N | N | H | $NH_2$ | J. Het. Chem. 10, 601(1973) |
| $CH_2$ | H | H | N | N | N | $NH_2$ | $NH_2$ | J. Med. Chem. 27 1416(1984) |
| $CH_2$ | H | OH | N | N | N | $NH_2$ | $NH_2$ | J. Med. Chem. 27, 670(1984) |
| $CH_2$ | OH | H | N | N | N | $NH_2$ | $NH_2$ | J. Pharm. Sci. 69 1019(1980) |
| $CH_2$ | H | OH | CH | CH | N | H | $NH_2$ | Nucleosides Nucleotides 3 345(1984) |
| $CH_2$ | H | OH | CH | CH | N | H | $NHCH_3$ | JACS 85 193 (1963) |
| $CH_2$ | H | OH | CBr | CH | N | H | $NH_2$ | JACS 86,1242 (1964) |

Additional starting materials can be prepared by the use of methods analogous to those described in Table 1 as well as other conventional methods as are well known and appreciated in the art.

The following example presents a typical synthesis as described by Scheme A. This example is understood to be illustrative only and is not intended to limit the scope of the present invention in any way.

EXAMPLE 1

(Z) and (E)-4', 5'-Didehydro-5'-deoxy-5'-fluoroadenosine

Step a: $N^6$-benzoyl-5'-deoxy-2',3'-0-isopropylidene-5',5'-adenosine.

Convert adenosine to its 2',3'-acetonide followed by benzoylation to the $N^6$-benzoyl derivative according to the procedure of Smrt et al. [Coll. Czech. Chem. Comm. 29, 224 (1964)].

Step b: $N^6,N^6$-Bis benzoyl-5-deoxy-2',3'-0-isopropylidene-5'-5'-(N,N'-diphenylethylenediamino)adenosine.

Convert $N^6$-benzoyl-5'-deoxy-2',3'-0-isopropylidene adenosine to $N^6$-benzoyl-5'-deoxy-2',3'-0-isopropylidene-5', 5'-(N,N'-diphenylethylenediamino)adenosine according to the procedure of Ranganathan et al. [J. Org. Chem. 39., 290 (1974)]. To 2.96 g of this product in 10 ml of pyridine, cooled in an ice bath, add 1.15 ml (9.9 mmol) of benzoyl chloride. Stir the mixture overnight at room temperature and pour into ice water. Extract the product into 100 ml of chloroform and dry with magnesium sulfate. Evaporate the solution on a rotary evaporator and add toluene. Repeat the evaporation in vacuo, and collect 4.07 g of a yellow foam. Percolate the product through a 40 mm×10 cm flash silica gel column with 4% ethyl acetate/96% dichloromethane. Combine and evaporate the appropriate fractions and collect a yellow oil. Dissolve the oil in ethanol and evaporate three times to yield a solid. Triturate the solid with 50 ml of ethanol and filter. Dry the solid in vacuo to give 2.67 g of the title compound [mp 135–138 degrees Celsius (°C.)].

NMR (CDCl$_3$, 90 MHz): δ1.30 (3H, S) 1.50 (3H, S), 3.3–3.7 (4H, m), 4.55 (1H, m), 5.1 (2H, d, J=2), 5.65 (1H, d, J=2), 6.1 (1H, S), 6.3–7.8 21H, M), 8.40 (1H, S).

Step b continued: $N^6,N^6$-Bis benzoyl-2',3'-0-isopropylidene adenosine-5'-aldehyde.

To 2.64 g (3.73 mmol) of $N^6,N^6$-Bis-benzoyl-5'-deoxy-2',3'- 0-isopropylidene-5',5'-(N,N'-diphenylethylenediamino)adenosine in 370 ml of dichloromethane at 0° C. add a solution of 1.56 g (8.2 mmol) p-toluenesulfonic acid monohydrate in 180 ml of acetone. Stir the mixture for 1.5 hours and filter. Evaporate the filtrate on a rotary evaporator and partition the residue between 200 ml of dichloromethane and water. Dry the dichloromethane solution with magnesium sulfate and evaporate to a foam. Dissolve 2.10 g of the foam in 200 ml of benzene and reflux in a Dean-Stark apparatus for one hour. Evaporate the solvent to give 2.06 g of the title compound. (NMR Spectrum reveals more than 80% of the product as aldehyde.)

NMR (CDCl$_3$, 90 MHz): δ1.40 (3H, S) 1.70 (3H, S), 4.65 (1H, S), 5.3 (1H, d, J=7), 5.45 (1H, broad d, J=7), 6.2 (1H, S), 7.2–7.8 (10H, m), 8.10 (1H, S), 8.45 (major) and 8.55 (1H together, two S). 9.3 (1H, S, CHO).

Step c: $N^6,N^6$-Bis-benzoyl-5'-deoxy-5',5'-difluoro-2',3'-0-isopropylideneadenosine.

Chromatograph 6.5 g of $N^6$, $N^6$-bis-benzoyl-2',3'-0-isopropylideneadenosine-5'-aldehyde on a 40 mm×7 cm flash silica gel column with 15% ethyl acetate/85% dichloromethane solvent. Combine and evaporate all fractions with UV—active material on Thin Layer Chromatography (TLC) to give 5.2 g of a foam. Reflux the foam in 200 ml of benzene for 2 hours and then evaporate and dry in vacuo to give 4.65 g of purified $N^6$, $N^6$-bis-benzoyl-2'3'- 0-isopropylideneadenosine-5'-aldehyde. Dissolve 3.90 g of the 5'-aldehyde in 25 ml of dichloromethane (distilled from calcium hydride) and to this solution add 3.2 ml (3 equivalents) of diethylaminosulfur trifluoride. Stir the mixture for 6 hours. Dilute the mixture with chloroform and pour into 50 ml of stirred saturated aqueous sodium bicarbonate. Extract the product into 400 ml of chloroform and dry with MgSO$_4$. Evaporate the solvent to give 3.60 g of a foam. Percolate the product through a 40 mm×12 cm silica gel flash column with 4% ethyl acetate/96% dichloromethane solvent. Isolate the title compound (738 mg) by TLC (R$_f$ 0.6 with 10% ethyl acetate/90% dichloromethane as solvent).

NMR (CDCl$_3$, 300 MHz): δ1.42 (3H, S) 1.65 (3H, S) 4.42–4.53 (1H, three m), 5.27 (1H, dd, J=2.7, 5.9), 5.39 (1H, dd, J=1.7, 6.0), 5.96 (1H, td, J=55, 4.5), 7.34–7.52 (6H, m), 7.85 (4H, d J=7.2), 8.15 (1H, S), 8.67 (1H, S).

19F-NMR (CDCl$_3$, 282 MHz, ppm from external CFCl$_3$) −54.87 (ddd, J=12.4, 55.2, 299.0) −50.71 (ddd, J=10, 55.2, 299.1)

MS (FAB - XENON) M+1=536

Anal: Calc'd for C$_{27}$H$_{23}$F$_2$N$_5$O$_5$. C 60.56, H 4.33 Found: C60.26, H.4.44

Step d: N$^6$ Benzoyl-4',5'-didehydro-2',3'-0-isopropylidene-5'-deoxy-5'-fluoroadenosine To 401 mg (0.75 mmol) of crushed N$^6$, N$^6$-Bis-benzoyl-5'-deoxy- 5',5'-difluoro-2',3'-0-isopropylideneadenosine and 335 mg (4 equivalents) of potassium t-butoxide under nitrogen add 2 ml of dimethylsulfoxide (distilled from calcium hydride). Stir the mixture under nitrogen for 21 hours. Quench with 4 ml of saturated ammonium chloride and extract with ethyl acetate to yield 274 mg of yellow oil. Percolate the oil through a 20 mm×15 cm flash column with 30% ethyl acetate/70% dichloromethane. Combine fractions that have two spots close together at Rf=0.55 (TLC with ethyl acetate as solvent). Evaporate these fractions to yield 183 mg of the title compound containing two isomers in a 2:1 ratio.

NMR (CDCl$_3$, 300 MHz): δ1.34 and 1.37 (minor) 3H together two S.), 1.49 (3H, s), 5.35–5.38 (1H, m), 5.56 and 5.90 (1H together; d, J=4 and m, resp.), 6.23 (broad s, minor) and 6.25 (1H together), 6.43 (d, J=74, major) and 6.81 (d, J=77; 1H together), 7.39–7.98 (6H, m), 8.646 (major) and 8.653 (minor; two s, 1H together), 9.05 (1H, broad, NH)

NMR $^{19}$F, 282 MHz, ppm from external CFCl$_3$): δ−158.94 (d, J=74 major), 174.4 (d, J=77, minor) MS: (CI) M+1=412.

Step e: N$^6$-Benzoyl-4',5'-didehydro-5'-deoxy-5'-fluoro adenosine

Dissolve 178 mg of N$^6$-benzoyl-4',5'-didehydro-2',3'-0-isopropylidene- 5'-deoxy-5'-fluoroadenosine (2:1 mixture of isomers) in 2 ml of cold trifluoroacetic acid-water (4:1). Stir the mixture at room temperature for 50 minutes and then evaporate on a rotary evaporator. Chromatograph the residue on a 20 mm×14 cm flash silica gel column with ethyl acetate as the solvent. Combine fractions to give 3 mg of the higher R$_f$ isomer (minor isomer), 58 mg of a mixture of isomers and 83 mg of the lower R$_f$ isomer (major isomer) of the title compound.

NMR (CD$_3$OD, higher R$_f$ isomer, 90 MHz): δ5.1 (2H, m), 6.35 (1H, d, J=6), (1H, D, J=74), 7.5–8.2 (5H, m), 8.63 (1H, s), 8.72 (1H, S).

NMR (CD$_3$OD, major lower R$_f$ isomer, 90 MHz): δ5.00–5.10 (2H, m), 6.37 (1H, d, J=7), 6.48 (1H, a, J=75), 7.54–8.19 (5H, m), 8.53 (1H, s), 8.62 (1H, s).

Step f: (Z)-4',5'-didehydro-5'-deoxy-5'-fluoroadenosine.

Dissolve 83 mg of N$^6$-benzoyl-4',5'-didehydro-5'-deoxy-5'-fluoroadenosine (lower R$_f$ isomer above) in absolute ethanol, evaporate and redissolve in 6 ml of ethanol. Bubble anhydrous ammonia through the ice cooled solution in a 20 mm×12 cm Carius tube. Seal the tube and remove the ice bath. After 14 hours at room temperature, open the tube and evaporate the solution to give 87 mg of crude product. Triturate in 1 ml of methanol and filter off the solid. Dry the product in vacuo to give 20 mg of the title compound (a white powder, softens at 100°–110° C. and melts at 225°–230° C.).

NMR (CD$_3$OD, 300 MHz): δ5.02–5.05 (2H, m), 6.28 (1H, d, J=F), 6.56 (1H, d, J=7.52), 8.21 (1H, s), 8.33 (1H, s).

$^{19}$F-NMR (282 MHz, ppm from external CFCl$_3$): −166.76 (d, J=75.2)

MS: (FAB-XENON) M+1=268

Step q: 4',5'-didehydro-5'-deoxy-5-fluoroadenosine, with E-isomer as major component.

Dissolve 58 mg of N$^6$-benzoyl-4',5'-didehydro-5'-deoxy-5'-fluoroadenosine (a mixture with the higher R$_f$ isomer being the major isomer) in 5 ml of absolute ethanol, and bubble ammonia through the ice cooled solution in a 20 mm×12 cm Carius tube for 3 three minutes. Seal the tube and remove the ice bath. After 15 hours at room temperature, open the tube and evaporate the solution. Dissolve the residue in 2 ml of methanol and chromatograph on a 20 mm×12 cm silica gel flash column. Eluted with ethyl acetate, followed by 10% methanol/90% ethyl acetate. Combine and evaporate fractions containing material at R$_f$ 0.23 (10% methanol/90% ethyl acetate) to yield 30 mg of product. Triturated in 12 mg of methanol and filter off the solid. Dry the product in vacuo to yield 16 mg of the title compound (an off-white powder). NMR indicates a 4:1 mixture of E-isomer to Z-isomer.

$^1$H-NMR (E-isomer CD$_3$OD 300 MHz): δ5.03–5.07 (2H, m) 6.21 (1H, d, J=6.3), 7.02 (1H, d, J=78.6), 8.20 (1H, s), 8.32 (1H, s).

$^{19}$F-NMR (E-isomer, CD$_3$OD, 282 MHz, ppm from ext. CFCl$_3$): −182.30 (d, J=78.5). MS: (CI) mH+=268.

The following specific compounds can be made by procedures analogous to those described above in Example 1:

(Z) or (E)-3-(5-deoxy-5-fluoro-.beta.-D-erythro-pent-4-enofuranosyl)- 5-fluoro-3H-1,2,3-triazolo[4,5-d]pyrimidin-7-amine (Z) or (E)-4',5'-didehydro-5'-deoxy-2,5'-difluoro-adenosine (Z) or (E)-9-(5-deoxy-5-fluoro-.beta.-D-threo-pent-4-enofuranosyl)- 9H-purin-6-amine (Z) or (E)-9(5-deoxy-5-fluoro-.beta.-D-threo-pent-4-enofuranosyl)- 9H-purin-6-amine

[1R-(1.alpha., 2.alpha., 3.beta., 5E or 5Z)-3-(4-amino-1H-imidazo[4,5-c]pyridin-1-yl)-5-(fluoromethylene)-1,2-cyclopentanediol (Z) or (E)-1-(5-deoxy-5-fluoro-.beta.-D-erythro-pent-4-enofuranosyl)- 1H-imidazo[4,5-c]pyridin-4-amine (Z) or (E)-3-(5-deoxy-5-fluoro-.beta.-D-erythro-pent-4-enofuranosyl- 3H-imidazo[4,5-b]pyridin-7-amine (Z) or (E)-9-(5-deoxy-5-fluoro-.beta.-D-erythro-pent-4-enofuranosyl-9H-purine (Z) or (E)-3-(5-deoxy-5-fluoro-.beta.-D-erythro-pent-4-enofuranosyl)- 1H-pyrazolo[4,3-d]pyrimidin-7-amine (Z) or (E)-2-chloro-4',5'-didehydro-5'-deoxy-5'-fluoroadenosine

[1R-(1.alpha., 2.alpha., 3.beta., 5E or 5Z)]-3-(6-amino-9H-purin- 9-yl)-5(fluoromethylene)-1,2-cyclopentanediol (Z) or (E)-4',5'-didehydro-2',5'-dideoxy-5'-fluoroadenosine (Z) or (E)-2-amino-4',5'-didehydro-5'-deoxy-5'-fluoroadenosine

[1R-(1.alpha., 2. alpha., 3.beta., 5E or 5Z)-3-(2,6-diamino-9H-purin-   9-yl)-5-(fluoromethylene)-1,2-cyclopentanediol

[1S-(1.alpha., 2E or 2Z, 4.beta.)]-4-(6-amino-9H-purin-9-yl)- 5-(fluoromethylene)cyclopentanol

[1R-(1.alpha., 2.beta., 3.beta., 5E or 5Z)]-3-(6-amino-9H-purin- 9-yl-)-5-(fluoromethylene)-1,2-cyclopentanediol

[1R-(1.alpha., 2.alpha., 3.beta., 5E or 5Z)]-3-(7-amino-3-H1,2,3-triazolo[4,5-d]pyrimidin-3-yl)-5-(fluoromethylene)-1,2-cyclopentanediol

[1S-(1.alpha., 2E or 2Z, 4.beta.)]-4-(7-amino-3H-1,2,3-triazolo[4,5-d]pyrimidin-3-yl)-2-(fluoromethylene)-cyclopentanol

[1R-(1.alpha., 2.beta., 3.beta., 5E or 5Z)-3-(5,7-diamino-3H-1,2,3-triazolo[4,5-d]pyrimidin-3-yl)-5-(fluoromethylene)-1,2-cyclopentanediol

[1R-(1.alpha., 2.alpha., 3.beta., 5E or 5Z)]-3-(5,7-diamino-3H-1,2,3-triazolo [4,5-d]pyrimidin-3-yl)-5-(fluoromethylene)-1,2-cyclopentanediol

[1R-(1.alpha., 2.alpha., 3.beta., 5E or 5Z)-3-(7-amino-3H-imidazo[4,5-b]pyridin-3-yl)-5-(fluoromethylene)-1,2-cyclopentanediol

[1S-(1.alpha., 2E 2Z, 4.beta.)]-4-(5,7-diamino-3H-1,2,3-triazolo[4,5-d]pyrimidin-3-yl)-2-(fluoromethylene)cyclopentanol (Z) or (E)-3-(5-deoxy-5-fluoro-.beta.-D-erythro-pent-4-enofuranosyl)-3H-1,2,3-triazolo[4,5-d]pyrimidine-5,7-diamine (Z) or (E)-N$^6$-methyl-4',5'-didehydro-5'-deoxy-5'-fluoroadenosine The aristeromycin/adenosine derivatives of the formula (1) wherein $X_1$ and $X_2$ are both halogen can be prepared according to conventional procedures and techniques well known and appreciated by one of ordinary skill in the art. A general synthetic procedures is set forth in Scheme B.

SCHEME B

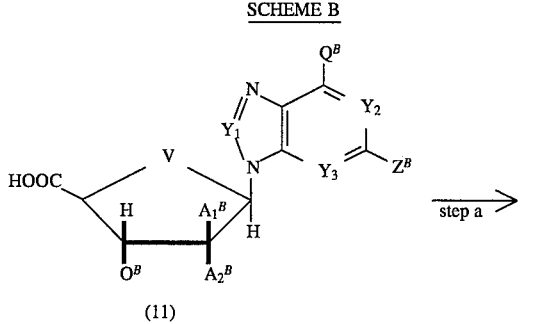

(11)

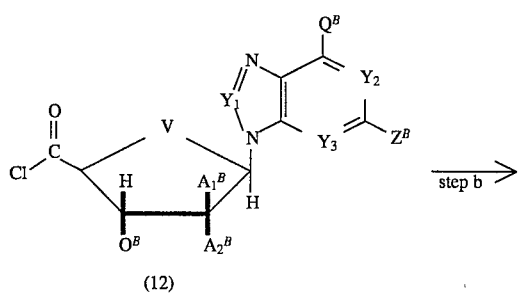

(12)

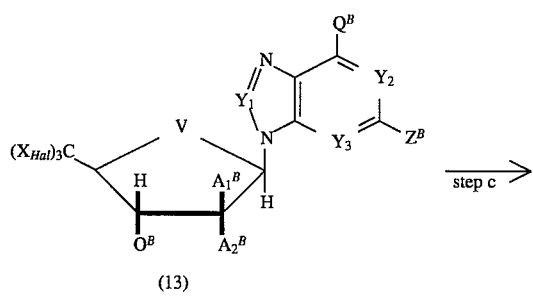

(13)

In step a, the carboxylic acid derivative (11) in which the appropriate amino and hydroxy groups have been blocked in a manner analogous to that described in Scheme A is converted to the acid chloride (12). The preferred reagent for this reaction is $SOCl_2$. The carboxylic acid derivative (11) can be prepared by oxidation of the corresponding alcohol according to the method of Harmon et al. [Chem. Ind. (London) 1141 (1969)].

The acid chloride derivative (12) is then converted to the tri-halo derivative (13). For example, in order to obtain the trifluoro derivative, (12) can be reacted with phenylsulfur trifluoride in 1,1,2-trichloro-1,2,2-trifluoroethane. In order to obtain the trichloro derivative (13), (12) can be reacted with phosphorus pentachloride or other reagents well known and appreciated in the art.

In step c, the trihalide (i.e., "$(X_{Hal})_3C$") derivative (13) is converted to the 5',5'-di-halo-4',5'-unsaturated derivative (14) in a reaction analogous to that described for Scheme A (step d). The preferred reagent for step c is potassium t-butoxide in dimethylsulfoxide.

The amino and hydroxy blocking groups can then be removed in a manner analogous to that described for Scheme A (steps e, f and g).

Starting materials for use in the general synthetic procedure outlined in Scheme B are readily available to one of ordinary skill in the art. For example, the starting materials for various compounds of formula (1) are listed in Table 2.

TABLE 2

Examples of Starting Materials for Scheme B
Compound of formula (1) wherein

| V | $A_1$ | $A_2$ | $Y_1$ | $Y_2$ | $Y_3$ | Z | Q | Source of Starting Material |
|---|---|---|---|---|---|---|---|---|
| O | H | OH | CH | N | CH | H | $NH_2$ | J. Med. Chem. 25, 626(1982) |
| O | H | OH | CH | N | N | H | $NH_2$ | Het. Chem., 14,195(1977) aristeromycin |
| O | H | OH | CH | CH | N | H | $NH_2$ | Nucleosides & Nucleotides, 1985, p. 625 |

Additional starting materials can be prepared by the use of methods analogous to those described in Tables 1 and 2 as well as other conventional methods as are well known and appreciated in the art.

The following example presents a typical synthesis as described by Scheme B. This example is understood to be illustrative only and is not intended to limit the scope of the present invention in any way.

EXAMPLE 2

4',5'-Didehydro-5'-deoxy-5',5'-difluoroadenosine

Steps a and b: 2',3'-0-Isopropylidene-5'-deoxy-5',5',5'-trifluoroadenosine

Combine 3.32 g (0.02 mole) of phenylsulfur trifluoride [prepared as described by Sheppard, JACS 84, 3058 (1962)] with 3.25 g (0.01 mole) of the acid chloride of 2',3'-0-isopropylidene adenosine-5'-carboxylic acid [prepared as described in Nucleic Acid Chemistry, Editors: Townsend and Tipson, John Wiley, 1978, p. 701] in 30 ml of 1,1,2-trichloro-1,2,2-trifluoroethane and heat overnight at 120° C. Add chloroform and pour the mixture into ice water. Extract the mixture with aqueous sodium bicarbonate. Evaporate the organic layer to give the crude product, and chromatograph on flash silica gel with ethyl acetate/methanol to give the title compound.

Step c: 4',5'-didehydro-2',3'-0-isopropylidene-5-deoxy-5',5'-difluoroadenosine

To 300 mg (0.9 mmole) of 2',3'-O-isopropylidine-5'-deoxy-5',5',5'-trifluoroadenosine and 410 mg (4 equivalents) of potassium t-butoxide add 2 ml of dimethyl sulfoxide and stir the mixture under nitrogen. Quench with water and extract with ethyl acetate to give the crude product. Chromatograph the crude product on silica gel with ethyl acetate to give the title compound.

De-blocking: 4',5'-didehydro-5'-deoxy-5',5'-difluoro adenosine

Treat 100 mg of 4',5'-didehydro-2',3'-0-isopropylidene-5'-deoxy-5',5'-difluoroadenosine with 2 ml of trifluoroacetic acid/water (4:1) for 1 hour and evaporate the solvent. Chromatograph on silica gel with ethyl acetate/methanol to give 60 mg of the title compound.

The following specific compounds can be made by procedures analogous to those described above in Example 2:

3-(5-deoxy-5,5-difluoro-.beta.-D-erythro-pent-4-enofuranosyl)- 5-fluoro-3H-1,2,3-triazolo[4,5-d]pyrimidin-7-amine,
4',5'-didehydro-5'-deoxy-2,5',5'-trifluoroadenosine
9-(5-deoxy-5,5-difluoro-.beta.-D-threo-pent-4-enofuranosyl)-9H-purin-6-amine
9(5-deoxy-5,5-difluoro-.beta.-D-threo-pent-4-enofuranosyl)- 9H-purin-6-amine
[1R-(1.alpha., 2.alpha., 3beta.)-3-(4-amino-1H-imidazo[4,5-c]pyridin-1-yl)-5-(difluoromethylene)-1,2-cyclopentanediol
1-(5-deoxy-5,5-fluoro-.beta.-D-erythro-pent-4-enofuranosyl)- 1H-imidazo[4,5-c]pyridin-4-amine
3-(5-deoxy-5,5-difluoro-.beta.-D-erythro-pent-4-enofuranosyl- 3H-imidazo[4,5-b]pyridin-7-amine
9-(5-deoxy-5,5-difluoro-.beta.-D-erythro-pent-4-enofuranosyl- 9H-purine
3-(5-deoxy-5,5-difluoro-.beta.D-erythro-pent-4-enofuranosyl)- 1H-pyrizolo[4,3-d]pyrimidin-7-amine
2-chloro-4',5'-didehydro-5'-deoxy-5',5'-difluoroadenosine
[1R-(1.alpha., 2.alpha., 3.beta.)]-3-(6-amino-9H-purin-9-yl)- 5-(difluoromethylene)-1,2-cyclopentanediol
4',5'-didehydro-2',5'-dideoxy-5',5'-difluoroadenosine
2-amino-4',5'-didehydro-5'-deoxy-5',5'-difluoroadenosine
[1R-(1.alpha., 2.alpha., 3.beta.)-3-(2,6-diamino-9H-purin-9-yl)-5-(difluoromethylene)-1,2-cyclopentanediol
[1S-(1.alpha., 2E, 4.beta.)]-4-(6-amino-9H-purin-9-yl)-5-(difluoromethylene)-cyclopentanol
[1R-(1.alpha., 2.beta., 3.beta.)]-3-(6-amino-9H-purin-9-yl-)-5-(difluoromethylene)-1,2-cyclopentanediol
[1R-(1.alpha., 2.alpha., 3.beta.)]-3-(7-amino-3H-1,2,3-triazolo[4,5-d]pyrimidin-3-yl)-5-(difluoromethylene)-1,2-cyclopentanediol
[1S-(1.alpha., 4.beta.)]-4-(7-amino-3H-1,2,3-triazolo[4,5-d] pyrimidin-3-yl-2-(difluoromethylene)-cyclopentanol
[1R-(1.alpha., 2.beta., 3.beta.)-3-(5,7-diamino-3H-1,2,3-trizolo[4,5-d]pyrinidin-3-yl)-5-(difluoromethylene)-1,2-cyclopentanediol
[1R-(1.alpha., 2.alpha., 3.beta.)]-3-(5,7-diamino-3H-1,2,3-triazolo[4,5-d]pyrimidin-3-yl)-5-(fluoromethylene)-1,2-cyclopentanediol
[1R-(1.alpha., 2.alpha., 3.beta.)-3-(7-amino-3H-imidazo[4,5-b]pyridin-3-yl)-5-(fluoromethylene-1,2-cyclopentanediol
[1S-(1.alpha., 4.beta.)]-4-(5,7-diamino-3H-1,2,3-triazolo[4,5-d]pyrimidin-3-yl)-2-(fluoromethylene)cyclopentanol
3-(5-deoxy-5-fluoro-.beta.-D-erythro-pent-4-enofuranosyl)-3H-1,2,3-triazolo[4,5-d]pyrinidine-5,7-diamine $N^6$-methyl-4',5'-didehydro-5'-deoxy-5'-fluoroadenosine An alternative procedure for preparing adenosine derivatives of the formula (1) wherein one or both of $X_1$ and $X_2$ are halogen i3 set forth in Scheme C. This method involves preparing the adenosyl base and ribosyl moieties separately and then effecting a condensation of the moieties.

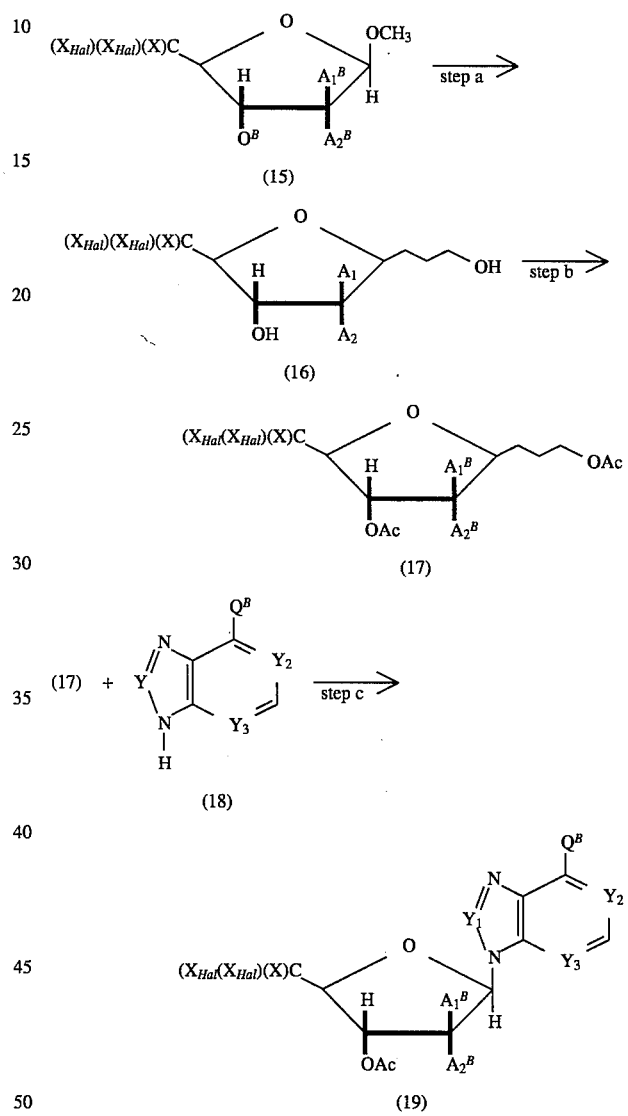

SCHEME C

Di or tri-halo- substituted ribosyl derivatives (15) are prepared according to standard techniques and procedures which are well known and appreciated by those of ordinary skill in the art. For example, these compounds can be prepared by methods analogous to that described by Sharma et al. (Tet. Lett. 1977, 3433) for the preparation of Methyl-5-deoxy-5,5-difluoro-2,3-isopropylideneribose.

These derivatives (15) are hydrolyzed in step a using an acid such as acetic acid. The hydrolyzed derivatives (16) are subsequently converted to the corresponding acetic acid esters (17) in step b by reaction with acetic anhydride in pyridine.

Procedures for making the adenine derivative (18) also involve standard techniques and procedures which are well known and appreciated by those of ordinary skill in the art.

The acetic acid ester (17) can be condensed with the appropriate adenine derivative (18) through a fusion reaction or through a condensation reaction in the presence of bis-trimethylsilylacetamide and a Lewis acid such as trimethylsilyltrifluoromethanesulfonate.

The condensed product (19) can then be de-blocked by hydrolysis and then appropriately blocked as described in Scheme A (step a) and further reacted to provide compounds of formula (1) as described in Scheme A (steps d through g).

Starting materials for use in the general synthetic procedure outlined in Scheme C are readily available to one of ordinary skill in the art. For example, the starting materials for various compounds of the formula (1) are listed in Table 3.

TABLE 3

Examples of Starting Materials for Scheme C
Compound of formula (1) wherein

| V | $A_1$ | $A_2$ | $Y_1$ | $Y_2$ | $Y_3$ | Z | Q | Source of Starting Material |
|---|---|---|---|---|---|---|---|---|
| O | H | OH | CH | N | N | Cl | $NH_2$ | 2-Chloroadenine and Tet. Lett. 1977, 3433 |
| O | H | OH | CH | N | N | H | $NH_2$ | Adenine |
| $CH_2$ | H | OH | CH | N | CH | H | $NH_2$ | 3-deazaadenine |

Additional starting materials can be prepared by the use of methods analogous to those described in Table 3 as well as other conventional methods as are well known and appreciated in the art.

The following example presents a typical synthesis as described by Scheme C. This example is understood to be illustrative only and is not intended to limit the scope of the present invention in any way.

EXAMPLE 3

$N^6,N^6$-Bisbenzoyl-5'-deoxy-5',5'-difluoro-2',3'-0-isopropylideneadenosine

Steps a and b: 5-deoxy-5,5-difluororibose and 5-deoxy-5,5-difluoro- 1,2,3-tri-0-acetylribose Dissolve 1.12 g (5 mmol) of methyl-5-deoxy-5,5-difluoro-2,3-isopropylideneribose (prepared as described by Sharma et al., Tet. Lett. 1977, 3433–3436), in 5 ml of 80% acetic acid and heat at 80° C. for 4 h followed by stirring overnight at room temperature. Evaporate the solvent, add toluene and evaporate again to give 5-deoxy-5,5-difluororibose. To the residue add 2.55 ml (2 mmol) of acetic anhydride and 10 ml of pyridine and stir the mixture was overnight. Subject the mixture to aqueous work-up followed by chromatography on flash silica gel (cyclohexane/dichloromethane) to give 5-deoxy-5,5-difluoro- 1,2,3-tri-o-acetylribose.

Step c: $N^6$-Benzoyl-5'-deoxy-5',5'-difluoro-2',3'-0-acetyl adenosine

To 1.06 g (4.4 mmol) of N-benzoyl adenine in 30 ml of acetonitrile add 3.2 ml (13 mmol) of bis-trimethylsilyl acetamide. Heat the mixture 0.5 h at reflux. Cool the mixture and add 1.00 g (3.4 mmol) of 5-deoxy-5,5-difluoro- 1,2,3-tri-0-acetylribose, followed by 1.5 ml of trimethylsilyl trifluoromethanesulfonate. Reflux the mixture for 5 hours, cool, and pour into a saturated sodium bicarbonate solution. Extract the product into chloroform, dry and evaporate to give the crude product. Chromatograph on flash silica gel to give the title compound.

De-blocking: 5'-deoxy-5',5'-difluoroadenosine

To 700 mg (1.5 mmol) of $N^6$-benzoyl-5'-deoxy-5',5'-difluoro- 2',3'-0-acetyladenosine in 20 ml of ethanol in a Carius tube add gaseous ammonia while cooling in ice. Seal the tube and allow it to stand overnight. Open the tube and evaporate the solvent. Chromatograph the product on flash silica gel, (ethyl acetate/methanol) to give the title compound.

Blocking: 5'-Deoxy-5',5'-difluoro-2',3'-0-isopropylidene adenosine

To 300 mg (1 mmol) of 5'-deoxy-5',5'-difluoroadenosine in 3 ml of acetone containing 215 mg (1.1 mmol) of p-toluenesulfonic acid monohydrate add 0.65 ml (4 mmol) of ethyl orthoformate while stirring. Stir the mixture for 2 h and then neutralize with dilute ammonium hydroxide. Partition the mixture between water and chloroform and evaporate the chloroform. Chromatograph the product on flash silica gel (ethyl acetate/methanol) to give the title compound.

Blocking: $N^6,N^6$-Bisbenzoyl-5'-deoxy-5',5'-difluoro-2',3'-0-isopropylideneadenosin To 160 mg of 5'-deoxy-5',5'-difluoro-2',3'-0-isopropylideneadenosine in 1 ml of pyridine add 0.17 ml of benzoyl chloride and stir the mixture overnight. Partition the mixture between water and chloroform. Evaporate the chloroform and chromatograph the residue on flash silica gel to give the title compound.

The further work-up of the title compound to yield compounds of formula (9) and (10) is described in Scheme A.

The following specific compounds can be made by procedures analogous to those described in Example 3:

(Z) or (E)-4'5'-didehydro-5'-deoxy-2,5'-difluoro-adenosine (Z) or (E)-1-(5-deoxy-5-fluoro-.beta.-D-erythro-pent-4-eno-furanosyl)- 1H-imidazo[4,5-c]pyridin-4-amine (Z) or (E)-3-(5-deoxy-5-fluoro-.beta.-D-erythro-pent-4-eno-furansyl- 3H-imidazo[4,5-b]pyridin-7-amine (Z) or (E)-9-(5-deoxy-5-fluoro-.beta.-D-erythro-pent-4-eno-furanosyl- 9H-purine (Z) or (E)-2-chloro-4',5'-didehydro-5'-deoxy-5'-fluoroadenosine (Z) or (E)-2-amino-4',5'-didehydro-5'-deoxy-5'-fluoroadenosine (Z) or (E)-$N^6$-methyl-4',5'-didehydro-5'-deoxy-5'-fluoroadenosine The following example presents a typical synthesis of a carbocyclic derivative. This example is understood to be illustrative only and is not intended to limit the scope of the present invention in any way.

EXAMPLE 4

[1R-(1.alpha., 2.alpha., 3.beta., 5E and 5Z)]-3-(6-amino- 9H-purin-9-yl)-5 (fluoromethylene)-1,2-cyclopentanediol

[1R-(1.alpha., 2.alpha., 3.beta.,]-3-(6-amino-9H-purin-9-yl)- 5-(hydroxymethyl)-1,2-cyclopentanediol-1,2-acetonide Combine aristeromycin [M. Ohno, et al; JACS, 105, 4049 (1983)] (1.0 g, 3.8 mmol) and anhydrous p-toluenesulfonic acid (2.0 g, 11.6 mmol) in acetone (60 mL) and stir for 0.5 hours. Add triethyl orthoformate (1.8 mL, 10.8 mmol) and stir for 2 hours. Pour the reaction mixture into a solution of ammonia in water prepared by mixing water (250 mL) and concentrated aqueous ammonia (25 mL). Evaporate the aqueous mixture in vacuo and chromatograph the residue obtained on silica gel eluting with 1/9 methanol/ethyl acetate to obtain a solid. Recrystallize the solid from ethyl acetate/ methanol to give the title compound [mp 217°–218° C.]. Elem. Anal. Calcd. for $C_{14}H_{19}N_5O_3$; C, 55.07, H, 6.27, N, 22.94. Found; C, 55.29, H, 6.45, N, 23.19.

[1R-(1.alpha., 2.alpha., 3.beta.,)]-3-[($N^6$-(N,N-dimethylaminomethyleneamino)- 9H-purin-9-yl]-5-(hydroxymethyl)-1, 2-cyclopentanediol-1,2-acetonide Combine [1R-(1.alpha., 2.alpha., 3.beta.,)]-3-1(6-amino-9H-purin-9-yl)-5(hydroxymethyl)-1,2-cyclopentanediol-1.2-acetonide (1.67 g, 5.47 mmol) and dimethylformamide dimethylacetal (2.6 g, 22 mmol) in dimethylformamide and stir for 16 hours at room temperature. Evaporate in vacuo to obtain the title compound as a residue.

[1R-(1.alpha., 2.alpha., 3.beta.,)]-3-[($N^6$-(N,N-dimethylaminomethyleneamino)- 9H-purin-9-yl]-5-(phenythiomethyl)-1,2-cyclopentanediol-1,2-acetonide Combine the residue obtained above with pyridine and add diphenyldisulfide (2.1 g, 9.8 mmol) and tributylphosphine (1.98 g, 9.8 mmol) and stir for 2 hours. Evaporate the reaction mixture in vacuo to obtain a residue.

[1R-(1.alpha., 2.alpha., 3.beta.,)]-3-(6-amino-9H-purin-9-yl]- 5-(phenythiomethyl)-1,2-cyclopentanediol-1,2-acetonide Combine the residue obtained above with methanol (50 mL) and cool in an ice bath before bubbling in ammonia until saturated. Seal the reaction vessel and warm to room temperature and stir for 24 hours. Evaporate in vacuo, dissolve in ethyl acetate (60 mL) and extract with 1M sodium hydroxide solution, 0.5M acetic acid solution, and a saturated solution of sodium chloride. Dry over magnesium sulfate, filter and evaporate in vacuo to give a residue. Triturate the residue with hexane (200 mL) to give the title compound as a solid. Recrystallize an analytical sample from ethyl acetate [mp 167°–169° C.]. Elem. Anal. Calcd. for $C_{20}H_{23}N_5O_2S \cdot 1.5H_2O$; C, 57.07, H. 6.11, N, 16.64. Found; C. 57.23, H, 5.71, N, 16.34.

[1R-(1.alpha., 2.alpha., 3.beta.,)]-3-(6-amino-9H-purin-9-yl]- 5-(phenylsulfinylmethyl)-1,2-cyclopentanediol-1,2-acetonide Combine [1R-(1.alpha., 2.alpha., 3.beta.,)]-3-(6-amino-9H-purin-9-yl]-5-(phenythiomethyl)-1,2-cyclopentanediol-1,2-acetonide (2.2 g, 5.53 mmol) and dichloromethane (50 mL) and cool in an ice bath. Add dropwise a solution of m-chloroperbenzoic acid (60%, 1.59 g, 5.53 mmol) in dichloromethane (10 mL). Extract the reaction mixture with a saturated solution of sodium bicarbonate, dry the organic layer over magnesium sulfate and potassium carbonate. Filter and evaporate in vacuo to give the title compound as a foam. $^1$H NMR (CDCl$_3$, mixture of diastereomers, 300 MHz) δ 1.27, 1.32, 1.51, 1.58 (s, 6H), 2.50–2.78 (m, 2H), 2.87–3.14 (m, 2H), 3.34 (dd, 1H, J=5.2 and 13.0 Hz), 4.49–4.65 (m, 2H), 5.15 (m, 1H), 7.81 (s, 1H), 8.30, 8.32 (s, 1H).

[1R-(1.alpha., 2.alpha., 3.beta.,)]-3-(6-amino-9H-purin-9-yl]-5-[(phenylthio)(fluoro)methyl]-1,2-cyclopentanediol-1, 2-acetonide Combine [1R-(1.alpha., 2.alpha., 3.beta.,)]-3-(6-amino-9H-purin- 9-yl]-5-(phenylsulfinylmethyl)-1,2-cyclopentanediol-1,2-acetonide (2.09 g, 5.05 mmol), diethylaminosulfur trifluoride (DAST) (2.7 g, 16.7 mmol) and antimony trichloride (10 mg) in chloroform (60 mL) and place the reaction vessel in an oil bath heated to 45° C. for 2 hours. Cool the reaction mixture to room temperature and pour into a saturated solution of sodium bicarbonate and extract with chloroform and dry over magnesium sulfate to obtain the title compound as a solution in chloroform. An analytical sample was evaporated and gives $^{19}$F NMR (CDCl$_3$)δ– 149.89 (dd, J=13.8 and 55.0 Hz) (60%), –154.62 (dd, J=17.5 and 55.0 Hz) (40%).

[1R-(1.alpha., 2.alpha., 3.beta.,)]-3-(6-amino-9H-purin-9-yl]- 5-[(phenylsulfinyl)(fluoro)methyl]-1,2-cyclopentanediol-1,2-acetonide Cool in an ice bath a solution in chloroform of [1R-(1.alpha., 2.alpha., 3.beta.,)]-3-(6-amino-9H-purin-9-yl]-5-[(phenylthio)(fluoro)methyl]-1,2-cyclopentanediol-1,2-acetonide obtain above. Add m-chloroperbenzoic acid (60%, 1.5 g, 5.0 mmol) in dichloromethane (10 mL). Extract the reaction mixture with a saturated solution of sodium bicarbonate, dry the organic layer over magnesium sulfate and potassium carbonate and evaporate in vacuo. Chromatograph on silica gel eluting with 5% methanol/dichloromethane, evaporate the product containing fractions to give the title compound as a foam. $^1$H NMR (CDl$_3$, mixture of four diastereomers, 300 MHz) δ1.26, 1.29, 1.32, 1.35 (s, 6H), 2.45–3.64 (m, 3H), 4.60–5.16 (m, 4H), 5.62–5.70 (m, 2H), 7.53–7.78 (m, 5H), 7.79, 7.82, 7.84 (s, 1H), 8.30, 8.31, 8.32, 8.35 (s, 1H); $^{19}$F NMR (CDCl$_3$) δ–183.56 (dd, J=23.7 and 48.2 Hz) (major diastereomer-53%), –188.86 (dd, J=16.9 and 48.2 Hz) (10%), –190.96 (dd, J=30.2 and 48.8 Hz) (25%), –195.12 (dd, J=20.6 and 48.2 Hz) (12%).

[1R-(1.alpha., 2.alpha., 3.beta., 5E and 5Z)]-3-(6-amino-9H-purin-9-yl)-5(fluoromethylene)-1,2-cyclopentanediol-1, 2,-acetonide Combine [1R-(1.alpha., 2.alpha., 3.beta.,)]-3-(6-amino-9H-purin-9-yl]-5-[(phenylsulfinyl)(fluoro)methyl]-1,2-cyclopentanediol-1,2-acetonide (1.31g, 3.04 mmol) and diethylisopropylamine (1.9 g, 15.0 mmol) in diglyme (20 mL) and heat to 120° C. for 4 hours. Evaporate the reaction mixture and obtain an oil. Chromatograph the oil on silica gel eluting 4% methanol/dichloromethane to give the title compound as a foam. E-isomer $^1$H NMR (CDCl$_3$, 300 MHz) δ1.35 (s, 3H), 1.55 (s, 3H), 3.00–3.26 (m, 2H), 4.90 (m, 1H), 5.03 (m, 1H), 5.90 (br s, 2H), 6.94 (d, 1H, J=82.0 Hz), 7.69 (s, 1H), 8.38 (s, 1H); $^{19}$F NMR (CDCl3) δ–124.55 (d, J=82.4 Hz); Z-isomer $^1$H NMR (CDCl$_3$, 300 MHz) δ1.36 (s, 3H), 1.55 (s, 3H), 3.03–3.32 (m, 2H), 4.91 (m, 1H), 5.02 (m, 1H), 5.14 (d, 1H, J=5.7 Hz) 5.67 (br s, 1H), 6.69 (d, 1H, J=81.5 Hz), 7.70 (s, 1H), 8.37 (s, 1H); $^{19}$F NMR (CDCl$_3$) δ–125.72 (d, J=82.4 Hz).

[1R-(1.alpha., 2.alpha., 3.beta., 5E and 5Z)]-3-(6-amino-9H-purin-9-yl)-5(fluoromethylene)-1,2-cyclopentanediol Combine water (0.2 mL) and [1R-(1.alpha., 2.alpha., 3.beta., 5E and 5Z)]-3-(6-amino- 9H-purin-9-yl)-5(fluoromethylene)-1,2-cyclopentanediol-1,2-acetonide (0.7 g, 2.29 mmol) in trifluoroacetic acid (15 mL). Stir at ambient temperature for 5 hours. Evaporate the reaction mixture add methanol (50 mL) and evaporate. Chromatograph on a Dekker column (Dowex 1×2 400 mesh, hydroxide form) eluting with methanol. Combine the Z-isomer containing fractions and evaporate. Recrystallize from acetone/ethyl acetate to give [1R-(1.alpha., 2.alpha., 3.beta., 5Z)]-3-(6-amino-9H-purin-9-yl)-5(fluoromethylene)- 1,2-cyclopentanediol [mp 207°–208° C.]. Elem. Anal. Calcd. for $C_{11}H_{12}FN_5O_2$; C, 49.81, H, 4.56, N, 26.40. Found; C, 49.74, H, 4.65, N, 25.24. Combine the crude E-isomer containing fractions and evaporate. Chromatograph on silica gel eluting eluting with 15% methanol/dichloromethane. Combine the E-isomer containing fractions and evaporate. Recrystallize from ethyl acetate to give [1R-(1.alpha., 2.alpha., 3.beta., 5E)]-3-(6-amino- 9H-purin-9-yl)-5(fluoromethylene)-1,2-cyclopentanediol [mp 200°–202° C.]. Elem. Anal. Calcd. for $C_{11}H_{12}FN_5O_2$; C, 49.81, H, 4.56, N, 26.40. Found; C, 49.62, H, 4.51, N, 26.05.

The following specific compounds can be made by procedures analogous to those described in Example 4:

[1R-(1.alpha., 2.alpha., 3.beta., 5E or 5Z)-3-(2,6-diamino-9H-purin-9-yl)-5-(fluoromethylene)-1,2-cyclopentanediol

[1S-(1.alpha., 4.beta., 2E or 2Z)]-4-(6-amino-9H-purin-9-yl)- 5-(fluoromethylene)cyclopentanol

[1R-(1.alpha., 2.beta., 3.beta., 5E or 5Z)]-3-(6-amino-9H-purin- 9-yl-)-5-(fluoromethylene)-1,2-cyclopentanediol

[1R-(1.alpha., 2.alpha., 3.beta., 5E or 5Z)]-3-(7-amino-3H-1,2,3-triazolo[4,5-d]pyrimidin-3-yl)-5-(fluoromethylene)-1,2-cyclopentanediol

[1S-(1.alpha., 4.beta., 2E or 2Z)]-4-(7-amino-3H-1,2,3-triazolo[4,5-d]pyrimidin-3-yl)-2-(fluoromethylene)-cyclopentanol

[1R-(1.alpha., 2.beta., 3.beta., 5E or 5Z)]-3-(5,7-diamino-3H-1,2,3-triazolo[4,5-d]pyrimidin-3-yl)-5-(fluoromethylene)- 1,2-cyclopentanediol

[1R-(1.alpha., 2.alpha., 3.beta., 5E or 5Z)]-3-(5,7-diamino-3H-1,2,3-triazolo [4,5-d]pyrimidin-3-yl)-5-(fluoromethylene)- 1,2-cyclopentanediol

[1R-(1.alpha., 2.alpha., 3.beta., 5E or 5Z)-3-(7-amino-3H-imidazo[4,5-b]pyridin-3-yl)-5-(fluoromethylene)-1,2-cyclopentanediol In another embodiment, the present invention provides a method of inhibiting AdoMet-dependent transmethylation activity in a patient in need thereof which comprises administration of a compound of the formula (1) in a therapeutically effective inhibitory amount. The term "therapeutically effective inhibitory amount" refers to an amount sufficient to inhibit the AdoMet-dependent transmethylation activity after single or multiple dose administration.

As used herein, the term "patient" refers to a warm-blooded animal such as a mammal which is afflicted with a particular disease state. It is understood that dogs, cats, rats, mice, horses, bovine cattle, sheep, and humans are examples of animals within the scope of the meaning of the term.

The compounds of formula (1) are believed to exert their inhibitory effect on AdoMet-dependent transmethylation by inhibition of AdoHcy Hydrolase thereby providing an increase in tissue levels of AdoHcy which in turn provides feedback inhibition of AdoMet-dependent transmethylation. However, it is understood that the present invention is not limited by any particular theory or proposed mechanism to explain its effectiveness in an end-use application.

As is well known and appreciated by those skilled in the art, various disease states, such as certain neoplastic disease states and viral infections, are characterized by excessive Adomet-dependent transmethylation activity. As used herein, the term "excessive" means a level of activity which allows the disease state to progress.

More specifically, the present invention provides a method for the treatment of a patient afflicted with a neoplastic disease state which is characterized by excessive AdoMet dependent transmethylation activity comprising the administration of a therapeutically effective antineoplastic amount of the compound of the formula (1). The term "neoplastic disease state" as used herein refers to an abnormal state or condition characterized by rapidly proliferating cell growth or neoplasm. Neoplastic disease states which are characterized by an excessive AdoMet-dependent transmethylation activity and for which treatment with a compound of formula (1) will be particularly useful include: Leukemias such as, but not limited to, acute lymphoblastic, chronic lymphocytic, acute myloblastic and chronic mylocytic; Carcinomas, such as, but not limited to, those of the cervix, oesophagus, stomach, small intestines, colon and lungs; Sarcomas, such as, but not limited to, oesteroma, osteosarcoma, lepoma, liposarcoma, hemangioma and hemangiosarcoma; Melanomas, including amelanotic and melanotic; and mixed types of neoplasias such as, but not limited to carcinosarcoma, lymphoid tissue type, folicullar reticulum, cell sarcoma and Hodgkins Disease.

A therapeutically effective antineoplastic amount of a compound of formula (1) refers to an amount which is effective, upon single or multiple dose administration to the patient, in controlling the growth of the neoplasm or in prolonging the survivability of the patient beyond that expected in the absence of such treatment. As used herein, "controlling the growth" of the neoplasm refers to slowing, interrupting, arresting or stopping its growth and metastases and does not necessarily indicate a total elimination of the neoplasm.

In addition, the present invention provides a method for the treatment of a patient afflicted with a viral infection which is characterized by excessive AdoMet-dependent transmethylation activity comprising the administration of a therapeutically effective antiviral amount of a compound of the formula (1). The term "viral infection" as used herein refers to an abnormal state or condition characterized by viral transformation of cells, vital replication and proliferation. Vital infections which are characterized by an excessive AdoMet dependent transmethylation activity and for which treatment with a compound of formula (1) will be particularly useful include: Retroviruses such as, but not limited to, HTLV-I, HTLV-II, human immunodeficiency viruses, HTLV-III (AIDS virus), and the like; RNA viruses such as, but not limited to, influenza type A, B, and C, mumps, measles, rhinovirus, dengue, rubella, rabies, hepatitis virus A, encephalitis virus, and the like; DNA viruses such as, but not limited to, herpes, vaccinia, pappiloma virus (wart), hepatitis virus B, and the like.

A therapeutically effective antiviral amount of a compound of formula (1) refers to an amount which is effective in controlling the virus. This vital control refers to slowing, interrupting, arresting or stopping the vital transformation of cells or the replication and proliferation of the virus and does not necessarily indicate a total elimination of the virus.

A therapeutically effective dose can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of the formula (1) is expected to vary from about 0.1 milligram per kilogram of body weight per day (mg/kg/day) to about 100 mg/kg/day. Preferred amounts are expected to vary from about 0.5 to about 10 mg/kg/day.

In an additional embodiment, the present invention relates to a method of treating a patient afflicted with a neoplastic disease state or a viral infection comprising administration of a therapeutically effective antineoplastic or antiviral amount of a compound of formula (1) wherein Q is $NH_2$ in conjunctive therapy with a therapeutically effective inhibitory amount of an Adenosine Deaminase (ADA) inhibitor. The term "conjunctive therapy" contemplates coadministration of (1) along with an ADA inhibitor at essentially the same time, or treatment of the patient with an ADA inhibitor prior to or after treatment with a compound of the formula (1). A therapeutically effective inhibitory amount of an ADA inhibitor is an amount effective in significantly inhibiting ADA in the patient.

ADA deaminates compounds of the formula (1) wherein Q is $NH_2$ and thereby degrades the active compounds to relatively inactive metabolites. When a compound of the formula (1) wherein Q is $NH_2$ and an ADA inhibitor are administered in conjunctive therapy, the dose will be less in amount or frequency of administration than that required when the compound of the formula (1) is administered alone.

Various pharmaceutically acceptable non-toxic ADA inhibitors can be used including, but not limited to, deoxycoformycin. A therapeutically effective inhibitory amount of the ADA inhibitor will vary from about 0.05 mg/kg/day to about 0.5 mg/kg/day and preferably will be from about 0.1 mg/kg/day to about 0.3 mg/kg/day. Deoxycoformycin is the preferred ADA inhibitor for use in conjunctive therapy with compounds of the formula (1) wherein Q is $NH_2$.

In effecting treatment of a patient afflicted with a disease state described above, a compound of formula (1) can be administered in any form or mode which makes the compound bioavailable in effective amounts, including oral and parenteral routes. For example, compounds of the formula (1) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. In addition, compounds of the formula (1) wherein Q is $NH_2$ can be administered as above in further combination with an ADA inhibitor. The compounds of the invention, while effective themselves, may be formulated and administered in the form of their pharmaceutically acceptable acid addition salts for purposes of stability, convenience of crystallization, increased solubility and the like.

In another embodiment, the present invention provides a pharmaceutical composition comprising a therapeutically effective amount of a compound of the formula (1) in admixture or otherwise in association with one or more pharmaceutically acceptable carriers or excipients. In addition, the present invention provides a pharmaceutical composition comprising a therapeutically effective amount of a compound of the formula (1) wherein Q is $NH_2$ and a therapeutically effective ADA inhibitory amount of an ADA inhibitor in admixture or otherwise in association with one or more pharmaceutically acceptable carriers or excipients. The term "therapeutically effective amounts" as applied to compounds of the formula (1) refers to effective inhibitory, antineoplastic, or antiviral amounts as appropriate.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of blass or plastic.

Any of the above described pharmaceutical compositions containing compounds of the formula (1) wherein Q is $NH_2$ may also contain a therapeutically effective inhibitory amount of an ADA inhibitor in admixture or otherwise in association with the above described ingredients.

As with any group of structurally related compounds which posses a particular generic utility, certain groups and configurations are preferred for compounds of the formula (1) in their end-use application.

With respect to the substituents $X_1$ and $X_2$, compounds wherein one of $X_1$ and $X_2$ is fluorine and the other is hydrogen are generally preferred. Compounds wherein $X_1$ is fluorine and $X_2$ is hydrogen are especially preferred.

With respect to the substituents $A_1$ and $A_2$, compounds wherein one of $A_1$ and $A_2$ is hydroxy and the other is hydrogen are generally preferred. Compounds wherein $A_1$ is hydrogen and $A_2$ is hydroxy are especially preferred.

The following are additional preferred embodiments: compounds wherein V is oxy, compounds wherein $Y_1$ is a CH group, compounds wherein $Y_2$ is nitrogen, compounds wherein $Y_3$ is nitrogen and compounds wherein Z is hydrogen.

Finally, with respect to Q, those compounds wherein Q is $NH_2$ or $NHCH_3$ are generally preferred with those wherein Q is $NH_2$ being especially preferred.

The following list identifies compounds of the formula (1) which are particularly preferred embodiments of the present invention:
(Z)-4',5'-didehydro-5'-deoxy-5'-fluoroadenosine
(Z)-4',5'-didehydro-5'-deoxy-2,5'-difluoroadenosine
(Z)-9(5-deoxy-5-fluoro-.beta.-D-threo-pent-4-enofuranosyl)- 9H-purin-6-amine
[1R-(.alpha., 2.alpha., 3.beta., 5E)-3-(4-amino-1H-imidazo[4,5-c]pyridin-1-yl)-5-(fluoromethylene-1,2-cyclopentanediol
(Z)-1-(5-deoxy-5-fluoro-.beta.-D-erythro-pent-4-enofuranosyl)- 1H-imidazo[4,5-c]pyridin-4-amine
[1R-(1.alpha., 2.alpha., 3.beta., 5E)]-3-(6-amino-9H-purin-9-yl)-5(fluoromethylene)-1,2-cyclopentanediol
(Z)-4',5'-didehydro-2',5'-dideoxy-5'-fluoroadenosine
4',5'-didehydro-5'-deoxy-5',5'-difluoroadenosine
4',5'-didehydro-5'-deoxy-2,5'-5'-trifluoroadenosine
9(5-deoxy-5,5-difluoro-.beta.-D-threo-pent-4-enofuranosyl)- 9H-purin-6-amine
[1R-(1.alpha., 2.alpha., 3.beta.)-3-(4-amino-1H-imidazo[4,5-c]pyridin-1-yl)-5-difluoromethylene)-1,2-cyclopentanediol
1-(5-deoxy-5,5-difluoro-.beta.-D-erythro-pent-4-enofuranosyl)- 1H-imidazo[4,5-c]pyridin-4-amine
[1R-(1.alpha., 2.alpha., 3.beta.)]-3-(6-amino-9H-purin-9-yl)- 5-(difluoromethylene)-1,2-cyclopentanediol
4',5'-didehydro-2',5'-dideoxy-5',5'-difluoroadenosine The above list is intended to be merely illustrative of particularly preferred embodiments of the present invention and it is understood that the list does not limit the scope of the invention in any way.

What is claimed:

1. A compound of the formula wherein

V is methylene, $X_1$ and $X_2$ are each independently hydrogen or halogen with the proviso that at least one of $X_1$ and $X_2$ is always a halogen atom, $A_1$ and $A_2$ are each independently hydrogen, halogen, or hydroxy with the provisos that where $A_1$ is hydroxy, $A_2$ is hydrogen, and that where $A_2$ is hydroxy, $A_1$ is hydrogen, $Y_1$ is nitrogen, a CH group, a CCl group, a CBr group or a $CNH_2$ group, $Y_2$ and $Y_3$ are each independently nitrogen or a CH group, Q is $NH_2$, NHOH, $NHCH_3$, or hydrogen, and Z is hydrogen, halogen, or $NH_2$; or a pharmaceutically acceptable salt thereof.

2. A compound of claim 1 wherein $X_1$ is fluorine and $X_2$ is hydrogen.

3. A compound of claim 1 wherein $X_2$ is fluorine and $X_1$ is hydrogen.

4. A compound of claim 1 wherein $X_1$ and $X_2$ are each fluorine.

5. A compound of claim 1 wherein $A_2$ is hydroxy.

6. A compound of claim 1 wherein $A_1$ is hydroxy.

7. A compound of claim 1 wherein $Y_1$ is a CH group.

8. A compound of claim 1 wherein $Y_2$ is nitrogen.

9. A compound of claim 1 wherein $Y_3$ is nitrogen.

10. A compound of claim 1 wherein Z is hydrogen.

11. The compound of claim 1 which is [1R-(.alpha., 2.alpha., 3.beta., 5E)]-3-(4-amino-1H-imidazo[4,5-c]pyridin- 1-yl)-5-(fluoromethylene-1,2-cyclopentanediol.

12. The compound of claim 1 which is [1R-(1.alpha., 2.alpha., 3.beta., 5E)]-3-(6-amino-9H-purin-9-yl)- 5(fluoromethylene)-1,2-cyclopentanediol.

13. The compound of claim 1 which is [1R-(1.alpha., 2.alpha., 3.beta., 5Z)]-3-(6-amino-9H-purin-9-yl)- 5(fluoromethylene)-1,2-cyclopentanediol.

14. The compound of claim 1 which is [1R-(1.alpha., 2.alpha., 3.beta.)]-3-(4-amino-1H-imidazo[4,5-c]pyridin-1-yl)- 5-difluoromethylene)-1,2-cyclopentanediol.

15. The compound of claim 1 which is [1R-(1.alpha., 2.alpha., 3.beta.)]-3-(6-amino-9H-purin-9-yl)-5-(difluoromethylene)- 1,2-cyclopentanediol.

16. The compound of claim 1 which is [1R-(1.alpha., 2.alpha., 3.beta., 5E or 5Z)]-3-(2,6-diamino-9H-purin-9-yl)- 5-(fluoromethylene)-1,2-cyclopentanediol.

17. The compound of claim 1 which is [1S-(1.alpha., 4.beta., 2E or 2Z)]-4-(6-amino-9H-purin-9-yl)-5-(fluoromethylene)cyclopentanol.

18. The compound of claim 1 which is [1R-(1.alpha., 2.beta., 3.beta., 5E or 5Z)]-3-(6-amino-9H-purin-9-yl-)-5-(fluoromethylene)- 1,2-cyclopentanediol.

19. The compound of claim 1 which is [1R-(1.alpha., 2.alpha., 3.beta., 5E or 5Z)]-3-(7-amino-3H-1,2,3-triazolo[4,5-d]pyrimidin-3-yl)-5-(fluoromethylene)-1,2-cyclopentanediol.

20. The compound of claim 1 which is [1S-(1.alpha., 4.beta., 2E or 2Z)]-4-(7-amino-3H-1,2,3-triazolo[4,5-d]pyrimidin-3-yl)-2-(fluoromethylene)-cyclopentanol.

21. The compound of claim 1 which is [1R-(1.alpha., 2.beta., 3.beta., 5E or 5Z)]-3-(5,7-diamino-3H-1,2,3-triazolo[4,5-d]pyrimidin-3-yl)-5-(fluoromethylene)-1,2-cyclopentanediol.

22. The compound of claim 1 which is [1R-(1.alpha., 2.alpha., 3.beta., 5E or 5Z)]-3-(5,7-diamino-3H-1,2,3-triazolo[ 4,5-d]pyrimidin-3-yl)-5-(fluoromethylene)-1,2-cyclopentanediol.

23. The compound of claim 1 which is [1R-(1.alpha., 2.alpha., 3.beta., 5E or 5Z)]-3-(7-amino-3H-imidazo[4,5-b] pyridin-3-yl)-5-(fluoromethylene)-1,2-cyclopentanediol.

24. A method of inhibiting AdoMet-dependent transmethylation activity in a patient in need thereof comprising administration of an inhibitory amount of a compound of the formula

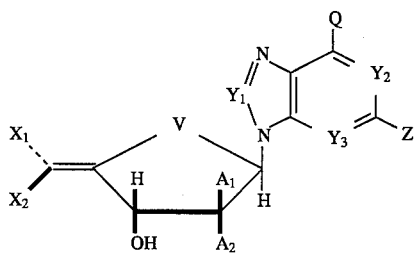

wherein
V is oxy or methylene,
$X_1$ and $X_2$ are each independently hydrogen or halogen with the proviso that at least one of $X_1$ and $X_2$ is always a halogen atom,
$A_1$ and $A_2$ are each independently hydrogen, halogen, or hydroxy with the provisos that where $A_1$ is hydroxy, $A_2$ is hydrogen, and that where $A_2$ is hydroxy, $A_1$ is hydrogen,
$Y_1$ is nitrogen, a CH group, a CCl group, a CBr group or a $CNH_2$ group,
$Y_2$ and $Y_3$ are each independently nitrogen or a CH group,
Q is $NH_2$, NHOH, $NHCH_3$, or hydrogen, and
Z is hydrogen, halogen, or $NH_2$; or a pharmaceutically acceptable salt thereof.

25. A method of treating a patient afflicted with a neoplastic disease state characterized by an excessive AdoMet-dependent transmethylation activity comprising the administration of an antineoplastic amount of a compound of the formula

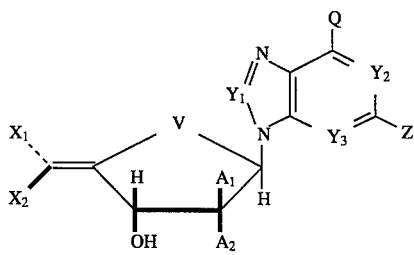

wherein
V is oxy or methylene,
$X_1$ and $X_2$ are each independently hydrogen or halogen with the proviso that at least one of $X_1$ and $X_2$ is always a halogen atom,
$A_1$ and $A_2$ are each independently hydrogen, halogen, or hydroxy with the provisos that where $A_1$ is hydroxy, $A_2$ is hydrogen, and that where $A_2$ is hydroxy, $A_1$ is hydrogen,
$Y_1$ is nitrogen, a CH group, a CCl group, a CBr group or a $CNH_2$ group,
$Y_2$ and $Y_3$ are each independently nitrogen or a CH group,
Q is $NH_2$, NHOH, $NHCH_3$, or hydrogen, and
Z is hydrogen, halogen, or $NH_2$; or a pharmaceutically acceptable salt thereof.

26. A method of treating a patient afflicted with a viral infection sensitive to SAH hydrolase inhibition comprising the administration of an antiviral amount of a compound of the formula

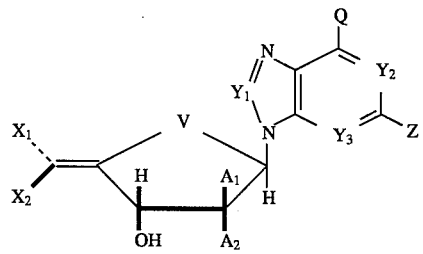

wherein
V is oxy or methylene,
$X_1$ and $X_2$ are each independently hydrogen or halogen with the proviso that at least one of $X_1$ and $X_2$ is always a halogen atom,
$A_1$ and $A_2$ are each independently hydrogen, halogen, or hydroxy with the provisos that where $A_1$ is hydroxy, $A_2$ is hydrogen, and that where $A_2$ is hydroxy, $A_1$ is hydrogen,
$Y_1$ is nitrogen, a CH group, a CCl group, a CBr group or a $CNH_2$ group,
$Y_2$ and $Y_3$ are each independently nitrogen or a CH group,
Q is $NH_2$, NHOH, $NHCH_3$, or hydrogen, and
Z is hydrogen, halogen, or $NH_2$; or a pharmaceutically acceptable salt thereof.

27. A method of inhibiting the growth of a neoplasm in a patient afflicted with a neoplastic disease state characterized by an excessive AdoMet-dependent transmethylation activity comprising administration of an antineoplastic amount of a compound of the formula wherein
V is oxy or methylene,
$X_1$ and $X_2$ are each independently hydrogen or halogen with the proviso that at least one of $X_1$ and $X_2$ is always a halogen atom,
$A_1$ and $A_2$ are each independently hydrogen, halogen, or hydroxy with the provisos that where $A_1$ is hydroxy, $A_2$ is hydrogen, and that where $A_2$ is hydroxy, $A_1$ is hydrogen,
$Y_1$ is nitrogen, a CH group, a CCl group, a CBr group or a $CNH_2$ group,
$Y_2$ and $Y_3$ are each independently nitrogen or a CH group,
Q is $NH_2$, NHOH, $NHCH_3$, or hydrogen, and
Z is hydrogen, halogen, or $NH_2$; or a pharmaceutically acceptable salt thereof.

28. A method of inhibiting a viral infection sensitive to SAH hydrolase inhibition in a patient afflicted therewith comprising administration of an antiviral amount of a compound of the formula

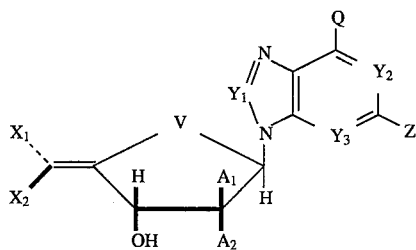

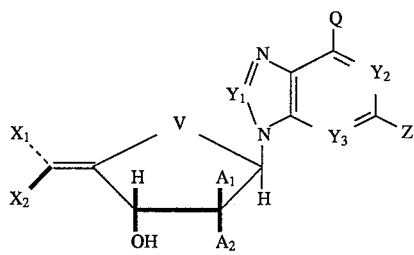

wherein

V is oxy or methylene, $X_1$ and $X_2$ are each independently hydrogen or halogen with the proviso that at least one of $X_1$ and $X_2$ is always a halogen atom, $A_1$ and $A_2$ are each independently hydrogen, halogen, or hydroxy with the provisos that where $A_1$ is hydroxy, $A_2$ is hydrogen, and that where $A_2$ is hydroxy, $A_1$ is hydrogen, $Y_1$ is nitrogen, a CH group, a CCl group, a CBr group or a $CNH_2$ group, $Y_2$ and $Y_3$ are each independently nitrogen or a CH group, Q is $NH_2$, NHOH, $NHCH_3$, or hydrogen, and Z is hydrogen, halogen, or $NH_2$; or a pharmaceutically acceptable salt thereof.

29. A method of inhibiting the growth of mammalian cells characterized by the presence of a transmethylation dependent disease state comprising exposing such cells to an inhibitory amount of a compound of the formula wherein V is oxy or methylene, $X_1$ and $X_2$ are each independently hydrogen or halogen with the proviso that at least one of $X_1$ and $X_2$ is always a halogen atom, $A_1$ and $A_2$ are each independently hydrogen, halogen, or hydroxy with the provisos that where $A_1$ is hydroxy, $A_2$ is hydrogen, and that where $A_2$ is hydroxy, $A_1$ is hydrogen, $Y_1$ is nitrogen, a CH group, a CCl group, a CBr group or a $CNH_2$ group, $Y_2$ and $Y_3$ are each independently nitrogen or a CH group, Q is $NH_2$, NHOH, $NHCH_3$, or hydrogen, and Z is hydrogen, halogen, or $NH_2$; or a pharmaceutically acceptable salt thereof.

30. In a method according to claim 25 wherein the compound is one wherein Q is $NH_2$, the improvement which comprises conjunctive therapy with an inhibitory amount of an adenosine deaminase (ADA) inhibitor.

31. In a method according to claim 26 wherein the compound is one wherein Q is $NH_2$, the improvement which comprises conjunctive therapy with an inhibitory amount of an adenosine deaminase (ADA) inhibitor.

* * * * *

UNITED STATES PATENT AND TRADEMARK OFFICE
CERTIFICATE OF CORRECTION

PATENT NO. : 5,521,162

DATED : May 28, 1996

INVENTOR(S) : Esa T. Jarvi; James R. McCarthy; Nellikunja J. Prakash

It is certified that error appears in the above-identified patent and that said Letters Patent is hereby corrected as shown below:

Column 1, Lines 28 & 29, Patent reads "vital" and should read --viral--.

Column 2, Line 9 Patent reads "anti-vital" and should read --anti-viral--.

Column 6, Line 66 Patent reads "1612" and should read --612--.

Column 6, Line 68 Patent reads "1601" and should read --601--.

Column 14, Line 4 Patent reads "I3" and should read --is--.

Column 18, Line 15 Patent reads "CdI$_3$" and should read --CDCl$_3$.

Column 20, Line 22 Patent reads "vital replication" and should read --viral replication--.

Column 20, Line 23 Patent reads "vital infections" and should read -- iral infections--.

Column 20, Line 36 Patent reads "vital control" and should read --viral control--.

Column 20, Line 37 Patent reads "vital transformation" and should read --viral transformation--.

Column 22, Line 62 Patent reads "blass" and should read --glass.

Signed and Sealed this

Sixth Day of October, 1998

Attest:

BRUCE LEHMAN

*Attesting Officer*      Commissioner of Patents and Trademarks